(12) United States Patent
Björkling

(10) Patent No.: US 7,304,066 B2
(45) Date of Patent: Dec. 4, 2007

(54) PYRIDYL CYANOGUANIDINE COMPOUNDS

(76) Inventor: Fredrik Björkling, Gotlandsgatan 3, S-25476 Helsingborg (SE)

( * ) Notice: Subject to any disclaimer, the term of this patent is extended or adjusted under 35 U.S.C. 154(b) by 593 days.

(21) Appl. No.: 10/476,856

(22) PCT Filed: May 24, 2002

(86) PCT No.: PCT/DK02/00353

§ 371 (c)(1), (2), (4) Date: Dec. 16, 2003

(87) PCT Pub. No.: WO02/094813

PCT Pub. Date: Nov. 28, 2002

(65) Prior Publication Data

US 2004/0220408 A1    Nov. 4, 2004

(51) Int. Cl.
C07D 213/72    (2006.01)
A61K 31/44    (2006.01)

(52) U.S. Cl. .............. 514/256; 546/152; 546/255; 546/272.7; 544/333; 514/314; 514/332; 514/341

(58) Field of Classification Search ............ 546/272.7, 546/152, 255; 514/256, 314, 332, 341; 544/333
See application file for complete search history.

(56) References Cited

U.S. PATENT DOCUMENTS 5,696,140 A * 12/1997 Bramm et al. ............ 514/353

FOREIGN PATENT DOCUMENTS

| WO | WO 94/06770 A1 | 3/1994 |
|---|---|---|
| WO | WO 98/54141 A1 | 12/1998 |
| WO | WO 98/54142 A1 | 12/1998 |
| WO | WO 98/54143 A1 | 12/1998 |
| WO | WO 98/54144 A1 | 12/1998 |
| WO | WO 98/54145 A1 | 12/1998 |
| WO | WO 00/61559 A1 | 10/2000 |
| WO | WO 00/61561 A1 | 10/2000 |

OTHER PUBLICATIONS

Sara Ekelund et al.: Biochemical Pharamcology, vol. 60, 2000, pp. 839-849, XP002902626.
Schou C et al.: Bioorganic & Medicinal Chemistry Letters, Oxford, vol. 7, No. 24, 1997, pp. 3095-3100, XP002079955.
Chen Jianyong et al.: Journal of China Pharmaceutical University, vol. 24, No. 4, 1993, pp. 202-204, SP002902627.

\* cited by examiner

*Primary Examiner*—Zinna N. Davis
(74) *Attorney, Agent, or Firm*—Birch, Stewart, Kolasch & Birch, LLP

(57) ABSTRACT

Compounds according to formula (I)

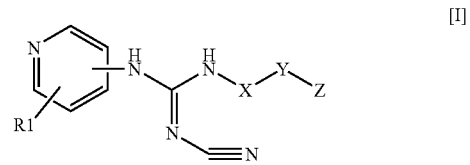

wherein R1 represents hydrogen, halogen or one or more straight or branched, saturated or unsaturated $C_{1-6}$ hydrocarbon radical, optionally substituted with halogen, hydroxy, cyano, nitro, carboxy, alkoxy, alkoxycarbonyl, alkylcarbonyl, formyl, amico, aminoalkyl, aminocarbonyl, alkylcarbonylamino, sulfo, aminosulfonyl, alkylsulfonylamino, hydroxysulfonyloxy, dihydroxyphosphinoyloxy or phosphono; X represents a straight or branched, saturated or unsaturated $C_{1-12}$ hydrocarbon diradical, optionaly substituted with halogen, hydroxy, cyano, nitro, carboxy, alkoxy, alkoxycarbonyl, alkylcarbonyl, formyl, amino, aminoalkyl, aminocarbonyl, alkylcarbonylamino, sulfo, aminosulfonyl, alkylsulfonylamino, hydroxysulfonyloxy, dihydroxyphosphinoyloxy or phosphono; Y represents a bond, O, C(O), S, S(O), $S(O)_2$, C(O)O, NH, C(O)NH, OC(O) or NHC(O); Z represents an aromatic or non-aromatic heterocyclic radical with 5-12 ring atoms, optionally substituted with halogen, hydroxy, cyano, nitro, alkoxy, alkoxycarbonyl, alkylcarbonyl, formyl, aminoalkyl or straight or branched, saturated or unsaturated $C_{1-4}$ hydrocarbon radical, optionally substituted with halogen, hydroxy, cyano, nitro, alkoxy, alkoxycarbonyl, alkylcarbonyl, formyl or aminoalkyl; provided that R1 is not attached to the nitrogen-atom in the pyridyl ring, and pharmaceutically acceptable salts, solvates, hydrates, N-oxides and prodrugs thereof are disclosed. The compounds are useful in therapy.

9 Claims, No Drawings

PYRIDYL CYANOGUANIDINE COMPOUNDS

This application is the national phase under 35 U.S.C. § 371 of PCT International Application No. PCT/DK02/00353 which has an International filing date of May 24, 2002, which designated the United States of America.

FIELD OF INVENTION

The present invention relates to novel pyridyl cyanoguanidine drugs and their inclusion in pharmaceutical compositions, as well as their use in the manufacture of medicaments.

BACKGROUND OF THE INVENTION

Pyridyl cyanoguanidines such as pinacidil (N-1,2,2-trimethylpropyl-N'-cyano-N"-(4-pyridyl)guanidine) were originally discovered to be potassium channel openers and were consequently developed as antihypertensive agents. Replacement of the side chain of pinacidil by longer aryl-containing side chains caused a loss of the antihypertensive activity, but such compounds were, on the other hand, found to show antitumour activity on oral administration in a rat model carrying Yoshida ascites tumours.

Different classes of pyridyl cyanoguanidines with antiproliferative activity are disclosed in, for instance, EP 660 823, WO 98/54141, WO 98/54143, WO 98/54144, WO 98/54145, WO 00/61559 and WO 00/61561. The structure-activity relationships (SAR) of such compounds are discussed in C. Schou et al., *Bioorganic and Medicinal Chemistry Letters* 7(24), 1997, pp. 3095-3100, in which the antiproliferative effect of a number of pyridyl cyanoguanidines was tested in vitro on different human lung and breast cancer cell lines as well as on normal human fibroblasts.

P-J V Hjarnaa et al., *Cancer Res.* 59, 1999, pp. 5751-5757, report on the results of further testing of a specific cyanoguanidine compound, i.e. N-(6-(4-chlorophenoxy)hexyl)-N'-cyano-N"-(4-pyridyl)guanidine in in vitro and in vivo tests. The compound exhibited a potency in vitro which was comparable to that of the reference cytostatic agents daunorubicin and paclitaxel, while showing considerably less antiproliferative activity on normal human endothelial cells. In in vivo tests using nude mice transplanted with human tumour cells, the compound showed substantial antitumour activity, also against tumour cells that were resistant to conventional anticancer drugs such as paclitaxel.

A successful drug requires a subtle balance between factors such as activity, bio-availability, toxicity, level of side-affects, solubility, etc. which allows for improved cyanoguanidine based drugs.

SUMMARY OF THE INVENTION

The present inventors have found that novel pyridyl cyanoguanidine compounds comprising a heterocyclic radical exhibit a surprisingly high anti-proliferative activity. Accordingly, the invention relates to compounds of formula I

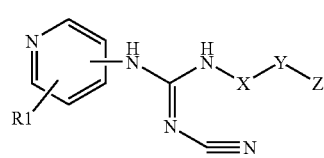

wherein R1 represents hydrogen, halogen or one or more straight or branched, saturated or unsaturated $C_{1-6}$ hydrocarbon radical, optionally substituted with halogen, hydroxy, cyano, nitro, carboxy, alkoxy, alkoxycarbonyl, alkylcarbonyl, formyl, amino, aminoalkyl, aminocarbonyl, alkylcarbonylamino, sulfo, aminosulfonyl, alkylsulfonylamino, hydroxysulfonyloxy, dihydroxyphosphinoyloxy or phosphono;

X represents a straight or branched, saturated or unsaturated $C_{1-12}$ hydrocarbon diradical, optionaly substituted with halogen, hydroxy, cyano, nitro, carboxy, alkoxy, alkoxycarbonyl, alkylcarbonyl, formyl, amino, aminoalkyl, aminocarbonyl, alkylcarbonylamino, sulfo, aminosulfonyl, alkylsulfonylamino, hydroxysulfonyloxy, dihydroxyphosphinoyloxy or phosphono;

Y represents a bond, O, C(O), S, S(O), $S(O)_2$, C(O)O, NH, C(O)NH, OC(O) or NHC(O);

Z represents an aromatic or non-aromatic heterocyclic radical with 5-12 ring atoms, optionally substituted with halogen, hydroxy, cyano, nitro, alkoxy, alkoxycarbonyl, alkylcarbonyl, formyl, aminoalkyl or a straight or branched, saturated or unsaturated $C_{1-4}$ hydrocarbon radical, optionally substituted with halogen, hydroxy, cyano, nitro, alkoxy, alkoxycarbonyl, alkylcarbonyl, formyl or aminoalkyl;

provided that R1 is not attached to the nitrogen-atom in the pyridyl ring;

and pharmaceutically acceptable salts, solvates, hydrates, N-oxides and prodrugs thereof.

The invention also relates to the use of a compound of formula I in therapy and to pharmaceutical compositions comprising a compound according to formula I.

The invention also relates to methods of treating or preventing diseases comprising administering to a patient an effective dose of a compound of formula I.

Furthermore, the invention relates to the use of compounds of formula I in the manufacture of medicaments.

DETAILED DESCRIPTION OF THE INVENTION

In the present context, the words "hydrocarbon" is intended to indicate a moiety comprising solely hydrogen and carbon, preferably comprising 1-18, e.g. 1-12, e.g. 1-6 carbon atoms. Examples of said hydrocarbon include methane, ethane, ethene, ethyne, butane, butene, butyne, iso-butane, tert.-butane, hexane, 1,3-di-methyl-hexane, octane, octene, nonyne, dodecane, dodecene, etc. The corresponding radical or di-radical is the moiety obtained by removing one or two, respectively, hydrogen atoms from the hydrocarbon.

The term "heterocyclic radical" is intended to indicate mono-cyclic rings with 1-3 heteroatoms selected from N, O and S, and fused bi-cyclic rings comprising 1-4 heteroatoms from the above selection. Examples include thienyl, furyl, pyranyl, isobenzofuranyl, chromenyl, pyrrolyl, imidazolyl, pyridyl, pyrimidinyl, indolizinyl, purinyl, quinolyl, naphthyridinyl, cinnonilyl, chromanyl, pyrrolidinyl, imidazolidinyl, piperidyl, piperazinyl, morpholinyl, oxazinyl, tetrahydrofuranyl, oxazolidinyl, tetrahydropyranyl, tetrazolyl, thiazolyl, pyrazolyl, oxazolyl, isooxazolyl, pyrazinyl, benzimadazolyl and benzofuranyl.

The term "halogen" is intended to indicate fluoro, chloro, bromo and iodo.

The term "pharmaceutically acceptable salt" is intended to indicate salts prepared by reacting compounds of formula I comprising acid or basic groups with suitable bases or acids, respectively. Examples of such acids are hydrochloric, hydrobromic, hydroiodic, sulfuric, nitric, acetic, phosphoric, lactic, meleic, phthalic, citric, propionic, benzoic, glutaric, gluconic, methanesulfonic, salicylic, succinic, tartaric, tolueneulfonic, sulfamic and fumaric acid. Examples of such bases are potassium hydroxide, sodium hydroxide, ammonia and amines.

The term "solvate" is intended to indicate a species formed by interaction between a compound, in casu a compound of formula I, and a solvent, e.g. alcohol, glycerol or water, wherein said species is in the solid form. When water is the solvent, the solvate is referred to a hydrate.

The term "N-oxide" is intended to indicate e.g. pyridyl N-oxide derivatives of the compounds of the invention. Such compounds may be prepared by oxidation of the pyridyl N by a suitable oxidising agent, e.g. 3-chloroperbenzoic acid in an inert solvent, e.g. dichlormethan.

The term "alkyl" is intended to indicate mono-radicals obtained from alkanes, preferably comprising 1-8 carbon atoms, such as methyl, ethyl, propyl, butyl, isobutyl, tert.-butyl, pentyl, hexyl and cyclohexyl.

The term "alkoxy" is intended to indicate a radical of the formula —OR, wherein R is alkyl as indicated above.

The term "alkoxycarbonyl" is intended to indicate a radical of the formula —C(O)—OR, wherein R is alkyl as indicated above.

The term "alkylcarbonyl" is intended to indicate a radical of the formula —C(O)—R, wherein R is alkyl as indicated above.

The term "aminoalkyl" is intended to indicate a radical of the formula —R—NR'$_2$, wherein R is alkyl as indicated above, and each R' independently represent alkyl as indicated above or hydrogen.

The term "aminocarbonyl" is intended to indicate a radical of the formula —C(O)—NR'$_2$, wherein each R' independently represent alkyl as indicated above or hydrogen.

The term "aminosulfonyl" is intended to indicate a radical of the formula —S(O)$_2$—NR'$_2$, wherein each R' independently represent alkyl as indicated above or hydrogen.

The term "alkylsulfonylamino" is intended to indicate a radical of the formula N(R')—S(O)$_2$—R, wherein R is alkyl as indicated above, and each R' independently represent alkyl as indicated above or hydrogen.

The term "amino" is intended to indicate a radical of the formula —NR'$_2$, wherein each R' independently represent alkyl as indicated above or hydrogen.

The term "prodrug" is intended to indicate a derivative of an active compound which does not, or does not necessarily, exhibit the physiological activity of the active compound, but which may be subjected to enzymatic cleavage such as hydrolysis in vivo so as to release the active compound on administration of the prodrug. The preparation of prodrugs of compounds of the present invention is disclosed in International Patent Application PCT/DK01/00750.

In a preferred embodiment of the invention, R1 represents hydrogen, halogen or one or more straight or branched, saturated or unsaturated $C_{1-6}$ hydrocarbon radical;

X represents a straight or branched, saturated or unsaturated $C_{1-12}$ hydrocarbon diradical;

Y represents O or C(O);

Z represents an aromatic or non-aromatic heterocyclic radical with 5-10 ring atoms.

In still another preferred embodiment of the invention, R1 represents hydrogen;

X represents a straight $C_{5-10}$ hydrocarbon diradical;

Y represents O;

Z represents an aromatic or non-aromatic heterocyclic radical with 5-10 ring atoms;

In a still further preferred embodiment, Z is selected from the list consisting of pyridyl, imidazolyl, quinolyl or pyrimidinyl.

Particular examples of compounds according to formula I include

N-[6-(3-pyridyl-oxy)-1-hexyl]-N'-cyano-N"-(4-pyridyl)-guanidine;

N-[6-(1-imidazolyl)-1-hexyl]-N'-cyano-N"-(4-pyridyl)-guanidine;

N-[6-(2-quinolyl-oxy)-1-hexyl]-N'-cyano-N"-(4-pyridyl)-guanidine;

N-[6-(3-pyridyl)-1-hexyl]-N'-cyano-N"-(4-pyridyl)-guanidine;

N-[6-(3-quinolyl)-1-hexyl]-N'-cyano-N"-(4-pyridyl)-guanidine;

N-[6-(5-pyrimidinyl)-1-hexyl]-N'-cyano-N"-(4-pyridyl)-guanidine;

Moreover, it is found that compounds selected from the list consisting of

3-[6-(N-tert-butoxycarbonylamino)-1-hexyl-oxy]-pyridine;

3-[6-amino-1-hexyl-oxy]-pyridine, hydrochloride;

3-[6-amino-1-hexyl-oxy]-pyridine;

1-[6-(N-tert-Butoxycarbonylamino)-1-hexyl]-imidazole;

1-(6-amino-1-hexyl)-imidazole, hydrochloride;

1-(6-amino-1-hexyl)-imidazole;

2-[6-(N-tert-Butoxycarbonylamino)-1-hexyl-oxy]-quinoline;

2-(6-amino-1-hexyl-oxy)-quinoline;

are particular useful in the preparation of compounds of formula I.

General Methods of Preparation

Compounds of formula I may be prepared by reacting a compound of formula II wherein R1 is as indicated in formula I, with a compound of formula III, wherein X, Y and Z are as indicated in formula I, see scheme.

The reaction may be performed in a suitable solvent, such as pyridine, optionally in the presence of a tertiary amine, such as triethylamine, and a catalyst, such as 4-(N,N-dimethylamino)-pyridine and at temperatures between room temperature and 100° C. During the reaction R1, X, Y and Z may temporarily contain suitable protection groups.

The compounds of formulae II and III are known from the literature or may be prepared by methods well known to persons skilled in the art.

In another embodiment a thiourea of the formula IV in which the substituents are as defined above in (I), and if necessary temporarily protected, is reacted with one or more equivalents of N,N'-dicyclohexylcarbodiimide (DCCD) and of cyanamide in an inert solvent, such as acetonitrile, at or above room temperature, yielding a compound of formula I, see scheme. The compounds of formulae IV may be prepared by methods well known to persons skilled in the art.

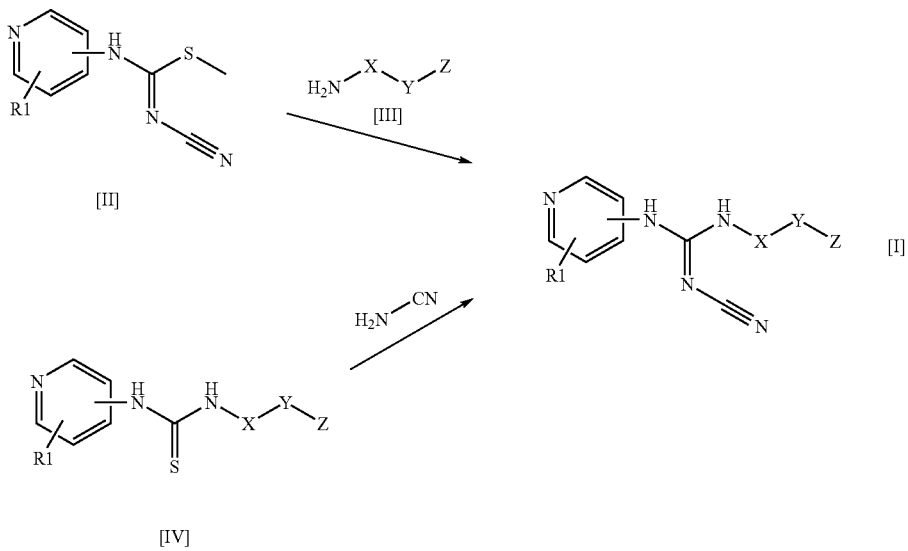

Pharmaceutical Formulations

In another aspect, the invention relates to pharmaceutical formulations of a compound of formula I. The formulations of the present invention, both for veterinary and for human medical use, comprise active ingredients in association with a pharmaceutically acceptable carrier(s) and optionally other therapeutic ingredient(s). The carrier(s) must be "acceptable" in the sense of being compatible with the other ingredients of the formulations and not deleterious to the recipient thereof.

Conveniently, the active ingredient comprises from 0.1-100% by weight of the formulation. Conveniently, a dosage unit of a formulation contain between 0.07 mg and 1 g of a compound of formula I.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations include e.g. those in a form suitable for oral (including sustained or timed release), rectal, parenteral (including subcutaneous, intraperitoneal, intramuscular, intraarticular and intravenous), transdermal, ophthalmic, topical, nasal or buccal administration.

The formulations may conveniently be presented in dosage unit form and may be prepared by any of the methods well known in the art of pharmacy, e.g as disclosed in Remington, *The Science and Practice of Pharmacy*, 20$^{th}$ ed., 2000. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units, such as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropyl methylcellulose, hydroxypropylcellulose, carbomers and polyvinylpyrrolidone. The active ingredients may also be administered in the form of a bolus, electuary or paste.

A tablet may be made by compressing or moulding the active ingredient optionally with one or more accessory ingredients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent.

Formulations for rectal administration may be may in the form of suppositories in which the compound of the present invention is admixed with low melting water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. The formulation may be conveniently sterilised by for instance filtration through a bacteria retaining filter, addition of sterilising agent to the formulation, irradiation of the formulation or heating of the formulation. Liposomal formulations as disclosed in e.g. *Encyclopedia of Pharmaceutical Technology*, vol. 9, 1994, are also suitable for parenteral administration.

Alternatively, the compound of formula I may be presented as a sterile, solid preparation, e.g. a freeze-dried powder, which is readily dissolved in a sterile solvent immediately prior to use.

Transdermal formulations may be in the form of a plaster or a patch.

Formulations suitable ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in *Encyclopedia of Pharmaceutical Technology*, vol.2, 1989, may also be used to present the active ingredient for ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops.

Formulations suitable for nasal or buccal administration include powder, self-propelling and spray formulations, such as aerosols and atomisers.

In addition to the aforementioned ingredients, the formulations of a compound of formula I may include one or more additional ingredients such as diluents, buffers, flavouring agents, colourant, surface active agents, thickeners, preservatives, e.g. methyl hydroxybenzoate (including anti-oxidants), emulsifying agents and the like.

In the systemic treatment using the present invention daily doses of from 0.001-500 mg per kilogram body weight, preferably from 0.002-100 mg/kg of mammal body weight, for example 0.003-20 mg/kg or 0.003 to 5 mg/kg of a compound of formula I is administered, typically corresponding to a daily dose for an adult human of from 0.01 to 37000 mg. However, the present invention also provides compounds and compositions intended for administration with longer intervals, e.g. every week, every three weeks or every month. In the topical treatment of dermatological disorders, ointments, creams or lotions containing from 0.1-750 mg/g, and preferably from 0.1-500 mg/g, for example 0.1-200 mg/g of a compound of formula I is administered. For topical use in ophthalmology ointments, drops or gels containing from 0.1-750 mg/g, and preferably from 0.1-500 mg/g, for example 0.1-200 mg/g of a compound of formula I is administered. The oral compositions are formulated, preferably as tablets, capsules, or drops, containing from 0.07-1000 mg, preferably from 0.1-500 mg, of a compound of formula I per dosage unit.

It has been found that cyanoguanidine derivatives are capable of modulating the activity of IκB kinase (abbreviated IKK in the following). By modulating the activity of IKK in the cells it is possible to control the level of activated NFκB in the cells. Such cyanoguanidines are therefore considered useful in the treatment of proliferative diseases and other conditions believed to be affected by the level of activated NFκB, e.g. inflammation.

NFκB is a member of the Rel family of transcription factors, which are ubiquitous in animal cells. Rel proteins can form dimers, the most common of which is designated NFκB. NFκB is a p50/p65 heterodimer which can activate transcription of genes containing the appropriate κB binding site. In non-stimulated cells, NFκB is maintained in the cytoplasm by an interaction with NFκB inhibiting proteins, the IκBS. In response to cell stimulation by e.g. anti-proliferative drugs or ionising radiation an IκB kinase complex (IKK) is rapidly activated and phosporylates two serine residues in the NFκB binding domain of IκB. The phophorylated IκB is then degraded by a 26S proteasome whereas NFκB is spared from degradation and translocates into the nucleus [Wang, *Science,* 274, 784-787, 1996, Cusak, *Cancer Research,* 60, 2323-2330, 2000; Karin, *Immunology,* 12, 2000, 85-98]. NFκB is thus always present in the cell, but in an inactivated form in non-stimulated cells. After translocation into the nucleus NFκB induces inter alia the anti-apoptotic genes c-IAP1, c-IAP2, TRAF1, TRAF2, Bfl-1/A1, Bcl-$X_L$ and Mn-SOD [Platel, *Oncogene,* 19, 2000, 4159-41699], which bring about resistance in the cells to apoptosis. This effect is referred to as the anti-apoptotic effect of NFκB. Anti-proliferative drugs and ionising radiation thus induce resistance in the cells to the treatments, which render them ineffective. Accordingly, activated NFκB is a key factor in induced resistance in e.g. cancer cells to anti-proliferative drugs and/or to ionising radiation. This is further supported by the fact that constitutively activated NFκB is found in cells from resistant cancer tumours [Patel, *Oncogene,* 19, 4159-4169, 2000]. Regardless of reduced resistance to any treatment, a reduction of the level of activated NFκB in the cell, e.g. by controlling the activity of IKK, will reduce the expression levels of genes encoding for anti-apoptotic factors inducing apoptosis in the cells [Schwartz, *Surgical Oncology,* 8, 1999, 143-153].

The role of activated NFκB is not restricted to preventing apoptosis. NFκB is also a critical activator of genes involved in inflammation and immunity. Activated NFκB induces the gene coding for cyclooxygenase 2 (COX2), which catalyses the synthesis of pro-inflammatory prostaglandins. Furthermore, at later stages in an inflammatory episode, COX2 catalyses the synthesis of the anti-inflammatory cyclopentenone prostaglandins. COX2 is also known to have anti-viral effects, which suggests that NFκB may also be a target in the therapy of inflammatory and viral diseases [Rossi, *Nature,* 403, 2000, 103-108]. NFκB is also responsible for the transcriptional regulation of genes important for many other vital cellular processes. NFκB e.g. regulates genes encoding cytokines and growth factors, adhesion molecules, acute phase reactants, receptors and chemoattractants [Schwartz, *Surgical Oncology,* 8, 1999, 143.153]. This is further supported by Rossi in *Nature,* 403, 103-108, 2000 where it is disclosed that another type of compound, namely cyclopentenone prostaglandins inhibits IκB kinase, and that this makes cyclopentenone prostaglandins potentially valuable in the treatment of cancers, inflammation and viral infections.

IκB is non-covalently bound to NFκB and masks its nuclear localisation signal, thereby preventing translocation into the nucleus. Various IκBs have been identified and e.g. IκBα and IκBβ are expressed in most cells where they bind to p65 Rel proteins, i.e. NFκB. Different IκB are phosphorylated by different factors allowing activation of NFκB in response to different stimuli.

The IκB kinase complex consist of three subunits, namely IKKα, IKKβ and IKKγ, with a combined molecular weight of 900 kDa. IKKα and IKKβ both exhibit IκB kinase activity and phophorylate IκB, whereas IKKγ is a regulatory subunit. IKKα is 85 kDa protein and IKKβ is a 87 kDa protein, and the two subunits show a large degree of homology. Whereas both IKKα and IKKβ are catalytically active, it has surprisingly been shown that only IKKβ is essential for IKK phosphorylation of IκB.

As described above, controlling the level of activated NFκB by controlling the activity of IKK may be useful as therapeutic intervention in the treatment of proliferative diseases, e.g. cancers and in particular resistant cancer forms. Controlling the activity of IKK may also be useful in the treatment of inflammatory or viral diseases. Controlling the activity of IKK may either be as a single agent therapy, or it may be part of a combination treatment with other treatments.

Apoptosis is a genetically encoded cell death programme characterised by an "active decision" by the cell based on information from its environment, its own internal metabolism, its developmental history, etc to die. Unlike cells undergoing necrosis, cells stimulated to enter apoptosis are often capable of survival, but opt to die for the good of the whole organism. Apoptosis is also different from necrosis in that necrosis is often associated with traumatised tissue and cell bursts, whereas the cells condense in the course of apoptosis, and are degraded intracellularly in a controlled manner [Tran, Science and Medicine, 6, 18-27, 1999; Williams, Trends Cell Biol., 2, 263-267, 1992].

In a preferred embodiment, the invention provides pharmaceutical compositions comprising a compound of formula I in combination with one or more other pharmacologically active compounds used in the treatment of proliferative diseases. Examples of compounds used in the treatment of proliferative diseases which may be used together with compounds of the present invention include 5-triazine derivatives such as altretamine; enzymes such as asparaginase; antibiotic agents such as bleomycin, dactinomycin, daunorubicin, doxorubicin, idarubicin, mitomycin, epirubicin and plicamycin; alkylating agents such as busulfan, carboplatin, carmustine, chlorambucil, cisplatin, cyclophosphamide, dacarbazine, ifosfamide, lomustine, mechlorethamine, melphalan, procarbazine and thiotepa; antimetabolites such as cladribine, cytarabine, floxuridine, fludarabine, fluorouracil, hydroxyurea, mercaptopurine, methotrexate, gemcitabin, pentostatin and thioguanine; antimitotic agents such as etoposide, paclitaxel, teniposide, vinblastine, vinorelbin and vincristine; hormonal agents, e.g. aromatase inhibitors such as aminoglutethimide, corticosteroids, such as dexamethasone and prednisone, and luteinizing hormone releasing hormone (LH-RH); antiestrogens such as tamoxifen, formestan and letrozol; antiandrogens such as flutamide; biological response modifiers, e.g. lymphokines such as aldesleukin and other interleukines; interferon such as interferon-α; growth factors such as erythropoietin, fligrastim and sagramostim; differentiating agents such as vitamin D derivatives, e.g. seocalcitol, and all-trans retinoic acid; immunoregulators such as levamisole; and monoclonal antibodies, tumour necrosis factor α and angiogenesis inhibitors. Finally, ionising radiation, although not readily defined as a compound, is heavily depended on in the treatment of neoplastic diseases, and may be combined with the compounds of the present invention. Due to the severe side effects often experienced by patients receiving antineoplastic treatment it is often desirable also to administer therapeutica which are not themselves anti-neoplastic, but rather help relieving the side effects. Such compounds include amifostin, leucovorin and mesna.

In particular, anti-proliferative compounds, such as paclitaxel, fluorouracil, etoposide, cyclophospamide, cisplatin, carboplatin, vincristine, gemcitabine, vinorelbine, chlorambucil, doxorubicin, melphalan and seocalcitol appear beneficial in the combination compositions of the present invention.

It is envisaged that the combination composition of the present invention may be provided as mixtures of the compounds or as individual compounds intended for simultaneous or sequential administration. It lies within the capabilities of a skilled physician or veterinarian to decide time intervals in a sequential administration regime.

In particular, proliferative diseases or conditions to be treated by the present method include a variety of cancers and neoplastic diseases or conditions including leukaemia, acute myeloid leukaemia, chronic myeloid leukaemia, chronic lymphatic leukaemia, myelodysplasia, multiple myeloma, Hodgkin's disease or non-Hodgkin's lymphoma, small or non-small cell lung carcinoma, gastric, intestinal or colorectal cancer, prostate, ovarian or breast cancer, head, brain or neck cancer, cancer in the urinary tract, kidney or bladder cancer, malignant melanoma, liver cancer, uterine or pancreatic cancer.

The invention also relates to the use of compounds of formula I, optionally together with other anti-neoplastic compounds, as indicated above, in the manufacture of medicaments. In particular, said medicament is intended to be used for the treatment of proliferative diseases, e.g. cancers as mentioned above.

METHODS OF PREPARATION

For $^1$H nuclear magnetic resonance (NMR) spectra (300 MHz) and $^{13}$C NMR (75.6 MHz) chemical shift values are quoted relative to internal tetramethylsilane (δ=0.00) or chloroform (δ=7.25) or deuteriochloroform (δ=76.81 for $^{13}$C NMR) standards. The value of a multiplet, either defined (singlet (s), doublet (d), triplet (t), quartet (q)) or not (broad (br)), at the approximate midpoint is given unless a range is quoted. The organic solvents used were anhydrous.

Preparation 1

3-[6-(N-tert-butoxycarbonylamino)-1-hexyl-oxy]-pyridine

3-Hydroxypyridine (262 mg) was added to a suspension of 60% sodium hydride (128 mg) in N,N-dimethylformamide (5 ml) and the mixture was stirred at 60° C. for 30 minutes. After cooling in ice a solution of N-(tert-butoxycarbonyl)-6-bromo-hexylamine (770 mg) (Helv. Chim. Acta 76 891 (1993) in N,N-dimethylformamide (3 ml) was added dropwise and stirring was continued overnight at room temperature. Ice and water were added and the mixture was extracted three times with diethyl ether. The organic phases were washed with saturated sodium chloride, dried and evaporated to leave a yellow oil which after purification by chromatography on silica gel with diethyl ether as eluent gave the desired compound as a colourless oil.

$^1$H NMR (CDCl$_3$) δ=8.29 (bs, 1H), 8.20 (m, 1H), 7.18 (m, 2H), 4.53 (bs, 1H), 4.00 (t, 2H), 3.13 (q, 2H), 1.80 (m, 2H), 1.44 (s, 9H), 1.60-1.30 (m, 6H)

Preperation 2

3-[6-amino-1-hexyl-oxy]-pyridine, hydrochloride

3-[6-(N-tert-Butoxycarbonylamino)-1-hexyl-oxy]-pyridine (180 mg) was treated with a large excess of hydrogen chloride in dietyl ether with stirring for 45 minutes followed by evaporation in vacuo. Trituration with diethyl ether, decantation and evaporation gave the title compound as a colourless powder.

¹H NMR (DMSO) δ=8.64 (d, 1H), 8.46 (d, 1H), 8.08 (m, 1H), 8.08 (bs, 3H), 7.88 (dd, 1H), 4.20 (t, 2H), 2.74 (m, 2H), 1.76 (m, 2H), 1.59 (m, 2H), 1.41 (m, 4H)

Preparation 3

3-[6-amino-1-hexyl-oxy]-pyridine

A solution of 3-[6-amino-1-hexyl-oxy]-pyridine, hydrochloride in water was made strongly alkaline with sodium hydroxide and ectracted twice with chloroform. The organic phase was dried and evaporated in vacuo to yield an oil which was used in the next step without further purification.

Preparation 4

1-[6-(N-tert-Butoxycarbonylamino)-1-hexyl]-imidazole

Imidazole (70 mg) and 1.4 M sodium methoxide (1 ml) were added to N,N-dimethylformamide (3 ml) and the mixture was stirred at room temperature for 30 minutes. A solution of N-(tert-butoxycarbonyl)-6-bromo-hexylamine (280 mg) in N,N-dimethylformamide (1 ml) was added and after heating at 80-90° C. for 30 minutes stirring was continued overnight at room temperature. Evaporation in vacuo followed by stirring with acetone and fitration gave a filtrate which after evaporation was purified by chromatography on silica gel with ethyl acetate/methanol (4:1) as eluent to yield the title compound as a colourless oil.
¹H NMR (CDCl₃) δ=7.46 (t, 1H), 7.05 (t, 1H), 6.90 (t, 1H), 4.60 (bs, 1H), 3.92 (t, 2H), 3.08 (q, 2H), 1.76 (m, 2H), 1.44 (s, 9H), 1.44 (m, 2H), 1.32 (m, 4H)

Preparation 5

1-(6-amino-1-hexyl)-imidazole, hydrochloride

Prepared as described in Preparation 2 but substituting 1-[6-(N-tert-butoxycarbonylamino)-1-hexyl]-imidazole for 3-[6-(N-tert-butoxycarbonylamino)-1-hexyl-oxy]-pyridine. Colourless crystals.
¹H NMR (DMSO) δ=14.99 (bs, 1H), 9.31 (t, 1H), 8.23 (bs, 3H), 7.86 (t, 1H), 7.71 (t, 1H), 4.22 (t, 2H), 2.73 (m, 2H), 1.81 (m, 2H), 1.58 (m, 2H), 1.36 (m, 2H), 1.23 (m, 2H)

Preparation 6

1-(6-amino-1-hexyl)-imidazole

Prepared as described in Preparation 3 but substituting 1-(6-amino-1-hexyl)-imidazole, hydrochloride for 3-[6-amino-1-hexyl-oxy]-pyridine, hydrochloride. Colourless oil.

Preparation 7

2-[6-(N-tert-Butoxycarbonylamino)-1-hexyl-oxy]-quinoline

This compound was prepared as described in Preparation 1 but substituting 2-hydroxyquinoline for 3-hydroxypyridine. The crude product was purified by chromatography on silica gel with ethyl acetate as eluent to yield the desired compound as a colourless oil.
¹H NMR (CDCl₃) δ=7.66 (d, 1H), 7.56 (m, 2H), 7.35 (bd, 1H), 7.22 (m, 1H), 6.70 (d, 1H), 4.57 (bs, 1H), 4.28 (m, 2H), 3.12 (m, 2H), 1.75 (m, 2H), 1.44 (s, 9H), 1.55-1.35 (m, 6H)

Preparation 8

2-(6-amino-1-hexyl-oxy)-quinoline

2-[6-(N-tert-Butoxycarbonylamino)-1-hexyl-oxy]-quinoline (480 mg) was treated with a large excess of hydrogen chloride in dietyl ether with stirring for 1 hour at room temperature. The crystalline product was isolated by filtration and redissolved in water whereafter the solution was made strongly alkaline with sodium hydroxide and extracted twice with chloroform. The organic phase was dried over potassium carbonate, filtered and evaporated to yield the title compound as a colourless oil.
¹H NMR (CDCl₃) δ=7.66 (d, 1H), 7.56 (m, 2H), 7.36 (m, 1H), 7.22 (m, 1H), 6.69 (d, 1H), 4.29 (m, 2H), 2.70 (t, 2H), 1.76 (m, 2H), 1.65 (bs, 2H), 1.45 (m, 6H)

EXAMPLE 1

N-[6-(3-pyridyl-oxy)-1-hexyl]-N'-cyano-N''-(4-pyridyl)-guanidine

A mixture of 3-[6-amino-1-hexyl-oxy]-pyridine (150 mg), S-methyl-N-cyano-N'-4-pyridyl-isothiourea (123 mg), triethylamine (0.18 ml), 4-(N,N-dimethylamino)-pyridine (3.5 mg) and pyridine (5 ml) was stirred overnight at 60° C. After cooling to room temperature the pyridine was removed by evaporation twice with toluene in vacuo and the residue was distributed between water and ethyl acetate. The organic phase was dried and evaporated to yield a crude product which was purified by chromatography on silica gel with ethyl acetate/methanol/aqueous ammonia (40:10:2.5) as eluent. The pure fractions were pooled and evaporated to give the title compound which crystallised from ethyl acetate.
¹H NMR (DMSO) δ=9.40 (bs, 1H), 8.38 (bd, 2H), 8.28 (d, 1H), 8.15 (dd, 1H), 7.86 (bt, 1H), 7.37 (m, 1H), 7.31 (dd, 1H), 7.22 (bs, 2H), 4.04 (t, 2H), 3.28 (q, 2H), 1.74 (m, 2H), 1.56 (m, 2H), 1.40 (m, 4H)

EXAMPLE 2

N-[6-(1-imidazolyl)-1-hexyl]-N'-cyano-N-(4-pyridyl)-guanidine

This compound was prepared as described in Example 1 but substituting 1-(6-amino-1-hexyl)-imidazole for 3-[6-amino-1-hexyl-oxy]-pyridine
¹H NMR (DMSO) δ=9.35 (bs, 1H), 8.39 (m, 2H), 7.86 (bt, 1H), 7.61 (t, 1H), 7.22 (m, 2H), 7.14 (t, 1H), 6.88 (t, 1H), 3.94 (t, 2H), 3.26 (q, 2H), 1.70 (m, 2H), 1.52 (m, 2H), 1.27 (m, 4H)

EXAMPLE 3

N-[6-(2-quinolyl-oxy)-1-hexyl]-N'-cyano-N''-(4-pyridyl)-guanidine

Prepared as described in Example 1 but substituting 2-(6-amino-1-hexyl-oxy)-quinoline for 3-[6-amino-1-hexyl-oxy]-pyridine.
¹H NMR (DMSO) δ=9.39 (bs, 1H), 8.38 (m, 2H), 7.90 (d, 1H), 7.87 (bt, 1H), 7.73 (m, 1H), 7.62 (m, 1H), 7.55 (bd, 1H), 7.30-7.10 (m, 3H), 6.61 (d, 1H), 4.23 (m, 2H), 3.27 (q, 2H), 1.61 (m, 2H), 1.54 (m, 2H), 1.39 (m, 4H)

EXAMPLE 4

N-[6-(3-pyridyl)-1-hexyl]-N'-cyano-N"-(4-pyridyl)-guanidine

Prepared as described in Example 1 but substituting 3-(6-amino-1-hexyl)-pyridine for 3-[6-amino-1-hexyl-oxy]-pyridine.

$^{13}$C NMR (DMSO) δ=157.0, 150.1, 149.5, 146.9, 145.8, 137.4, 135.6, 123.3, 116.4, 114.5, 41.7, 31.9, 30.4, 28.5, 28.1, 25.8

EXAMPLE 5

N-[6-(3-quinolyl)-1-hexyl]-N'-cyano-N"-(4-pyridyl)-guanidine

Prepared as described in Example 1 but substituting 3-(6-amino-1-hexyl)-quinoline for 3-[6-amino-1-hexyl-oxy]-pyridine.

$^{13}$C NMR (DMSO) δ=157.0, 151.9, 150.1, 146.2, 145.7, 135.0, 133.7, 128.5, 128.4, 127.7, 127.5, 126.4, 116.4, 114.5, 41.7, 32.1, 30.3, 28.5, 28.1, 25.8

EXAMPLE 6

N-[6-(5-pyrimidinyl)-1-hexyl]-N'-cyano-N"-(4-pyridyl)-guanidine

Prepared as described in Example 1 but substituting 5-(6-amino-1-hexyl)-pyrimidine for 3-[6-amino-1-hexyl-oxy]-pyridine.

$^{13}$C NMR (DMSO) δ=157.1, 156.6, 156.2, 149.9, 145.5, 135.3, 116.3, 114.4, 41.7, 29.9, 29.2, 28.4, 28.0, 25.7

The invention claimed is:

1. A compound according to formula I

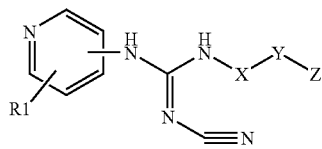

[I]

wherein R1 represents hydrogen, halogen or one or more straight or branched, saturated or unsaturated $C_{1-6}$ hydrocarbon radical, optionally substituted with halogen, hydroxy, cyano, nitro, carboxy, alkoxy, alkoxycarbonyl, alkylcarbonyl, formyl, amino, aminoalkyl, aminocarbonyl, alkylcarbonylamino, sulfo, aminosulfonyl, alkylsulfonylamino, hydroxysulfonyloxy, dihydroxyphosphinoyloxy or phosphono;

X represents a straight or branched, saturated or unsaturated $C_{4-12}$ hydrocarbon diradical, optionally substituted with halogen, hydroxy, cyano, nitro, carboxy, alkoxy, alkoxycarbonyl, alkylcarbonyl, formyl, amino, aminoalkyl, aminocarbonyl, alkylcarbonylamino, sulfo, aminosulfonyl, alkylsulfonylamino, hydroxysulfonyloxy, dihydroxyphosphinoyloxy or phosphono;

Y represents a bond, O, C(O), S, S(O), S(O)$_2$, C(O)O, NH, C(O)NH, OC(O) or NHC(O);

Z represents an aromatic heterocyclic radical with 5-12 ring atoms, optionally substituted with halogen, hydroxy, cyano, nitro, alkoxy, alkoxycarbonyl, alkylcarbonyl, formyl, aminoalkyl or a straight or branched, saturated or unsaturated $C_{1-4}$ hydrocarbon radical, optionally substituted with halogen, hydroxy, cyano, nitro, alkoxy, alkoxycarbonyl, alkylcarbonyl, formyl or aminoalkyl;

provided that R1 is not attached to the nitrogen-atom in the pyridyl ring;

or pharmaceutically acceptable salts, solvates, hydrates, N-oxides or prodrugs thereof.

2. A compound according to claim 1 wherein R1 represents hydrogen, halogen or one or more straight or branched, saturated or unsaturated $C_{1-4}$ hydrocarbon radical;

X represents a straight or branched, saturated or unsaturated $C_{4-12}$ hydrocarbon diradical;

Y represents a bond, O or C(O);

Z represents an aromatic heterocyclic radical with 5-10 ring atoms.

3. A compound according to claim 1, wherein R1 represents hydrogen;

X represents a straight $C_{5-10}$ hydrocarbon diradical;

Y represents O;

Z represents an aromatic heterocyclic radical with 5-10 ring atoms.

4. A compound according to claim 1 wherein Z represents pyridyl, imidazolyl, quinolyl or pyrimidinyl.

5. A compound according to claim 1 selected from the group consisting of

N-[6-(3-pyridyl-oxy)-1-hexyl]-N'-cyano-N"-(4-pyridyl)-guanidine;

N-[6-(1-imidazolyl)-1-hexyl]-N'-cyano-N"-(4-pyridyl)-guanidine;

N-[6-(2-quinolyl-oxy)-1-hexyl]-N'-cyano-N"-(4-pyridyl)-guanidine;

N-[6-(3-pyridyl)-1-hexyl]-N'-cyano-N"-(4-pyridyl)-guanidine;

N-[6-(3-quinolyl)-1-hexyl]-N'-cyano-N"-(4-pyridyl)-guanidine; and

N-[6-(5-pyrimidinyl)-1-hexyl]-N'-cyano-N"-(4-pyridyl-guanidine.

6. A pharmaceutical composition comprising a compound according to any of claims 1-5, optionally together with other pharmacologically active ingredients, and together with pharmaceutically acceptable excipients.

7. A composition according to claim 6 in dosage unit form.

8. A composition according to claim 6 wherein said other pharmacologically active compound is selected from the group consisting of paclitaxel, fluorouracil, etoposide, cyclophospamide, cisplatin, carboplatin, vincristine, gemcitabine, vinorelbine, chlorambucil, doxorubicin, melphalan and seocalcitol.

9. A composition according to claim 7 wherein said other pharmacologically active compound is selected from the group consisting of paditaxel, fluorouradl, etoposide, cydophospamide, cisplatin, carboplatin, vincristine, gerncitabine, vinorelbine, chlorambucil, doxorubicin, melphalan and seocaldtol.

* * * * *